(12) United States Patent
Forsberg (10) Patent No.: US 7,618,436 B2
(45) Date of Patent: *Nov. 17, 2009

(54) TISSUE PUNCTURE CLOSURE DEVICE WITH SCROLL GEAR TRANSMISSION TAMPING SYSTEM

(75) Inventor: Andrew Thomas Forsberg, Minneapolis, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 541 days.

This patent is subject to a terminal disclaimer.

(21) Appl. No.: 11/103,730

(22) Filed: Apr. 12, 2005

(65) Prior Publication Data

US 2006/0229674 A1    Oct. 12, 2006

(51) Int. Cl.
*A61B 17/08*   (2006.01)
*A61D 1/00*    (2006.01)

(52) U.S. Cl. .................................. 606/213; 74/113

(58) Field of Classification Search ............... 74/89.18, 74/89.11, 431, 434, 437, 113; 185/9, 10, 185/37, 39, 45; 606/169, 171, 213
See application file for complete search history.

(56) References Cited

U.S. PATENT DOCUMENTS

| | | | |
|---|---|---|---|
| 466,923 A * | 1/1892 | Price | ........................... 74/437 |
| 3,952,607 A * | 4/1976 | Ring | ........................... 74/393 |
| 4,317,445 A | 3/1982 | Robinson | |
| 4,744,364 A | 5/1988 | Kensey | |
| 4,890,612 A | 1/1990 | Kensey | |
| 5,021,059 A | 6/1991 | Kensey et al. | |
| 5,061,274 A | 10/1991 | Kensey | |
| 5,108,421 A | 4/1992 | Fowler | |
| 5,192,302 A | 3/1993 | Kensey et al. | |
| 5,209,134 A * | 5/1993 | Nguyen et al. | ................. 74/437 |
| 5,222,974 A | 6/1993 | Kensey et al. | |
| 5,282,827 A | 2/1994 | Kensey et al. | |
| 5,290,310 A | 3/1994 | Makower et al. | |
| 5,292,332 A | 3/1994 | Lee | |
| 5,304,184 A | 4/1994 | Hathaway et al. | |
| 5,306,254 A | 4/1994 | Nash et al. | |
| 5,312,435 A | 5/1994 | Nash et al. | |
| 5,320,639 A | 6/1994 | Rudnick | |
| 5,324,306 A | 6/1994 | Makower et al. | |
| 5,326,350 A | 7/1994 | Li | |

(Continued)

FOREIGN PATENT DOCUMENTS

WO    WO0078226    * 12/2000

OTHER PUBLICATIONS

International Search Report and Written Opinion from corresponding International Application No. PCT/US05/46583, dated Aug. 8, 2007 (7 pages).

*Primary Examiner*—(Jackie) Tan-Uyen T. Ho
*Assistant Examiner*—Dianne Dornbusch
(74) *Attorney, Agent, or Firm*—Holland & Hart (57) ABSTRACT

Methods and apparatus for sealing a puncture or incision formed percutaneously in tissue separating two internal portions of the body of a living being with an anchor, a sealing plug and a filament connecting the anchor and sealing plug are disclosed. The methods and apparatus provide for automatic tamping of the sealing plug. In addition, a scroll gearset changes gear ratio as it transduces a retraction force into a sealing plug tamping force.

28 Claims, 6 Drawing Sheets

U.S. PATENT DOCUMENTS

| | | |
|---|---|---|
| 5,334,216 A | 8/1994 | Vidal et al. |
| 5,342,393 A | 8/1994 | Stack |
| 5,368,601 A | 11/1994 | Sauer et al. |
| 5,383,896 A | 1/1995 | Gershony et al. |
| 5,383,897 A | 1/1995 | Wholey |
| 5,383,899 A | 1/1995 | Hammerslag |
| RE34,866 E | 2/1995 | Kensey et al. |
| 5,391,183 A | 2/1995 | Janzen et al. |
| 5,403,328 A | 4/1995 | Shallman |
| 5,403,329 A | 4/1995 | Hinchcliffe |
| 5,405,354 A | 4/1995 | Sarrett |
| 5,411,520 A | 5/1995 | Nash et al. |
| 5,417,699 A | 5/1995 | Klein et al. |
| 5,431,639 A | 7/1995 | Shaw |
| 5,431,666 A | 7/1995 | Sauer et al. |
| 5,437,631 A | 8/1995 | Janzen |
| 5,443,481 A | 8/1995 | Lee |
| 5,462,561 A | 10/1995 | Voda |
| 5,486,195 A | 1/1996 | Myers et al. |
| 5,496,332 A | 3/1996 | Sierra et al. |
| 5,496,335 A | 3/1996 | Thomason et al. |
| 5,507,744 A | 4/1996 | Tay et al. |
| 5,507,758 A | 4/1996 | Thomason et al. |
| 5,527,322 A | 6/1996 | Klein et al. |
| 5,531,759 A | 7/1996 | Kensey et al. |
| 5,545,178 A | 8/1996 | Kensey et al. |
| 5,549,633 A | 8/1996 | Evans et al. |
| 5,571,181 A | 11/1996 | Li |
| 5,591,205 A | 1/1997 | Fowler |
| 5,593,422 A | 1/1997 | Muijs Van de Moer et al. |
| 5,601,603 A | 2/1997 | Illi |
| 5,613,974 A | 3/1997 | Andreas et al. |
| 5,620,461 A | 4/1997 | Muijs Van De Moer et al. |
| 5,626,601 A | 5/1997 | Gershony et al. |
| 5,643,318 A | 7/1997 | Tsukernik et al. |
| 5,645,566 A | 7/1997 | Brenneman et al. |
| 5,649,959 A | 7/1997 | Hannam et al. |
| 5,653,730 A | 8/1997 | Hammerslag |
| 5,662,681 A | 9/1997 | Nash et al. |
| 5,665,106 A | 9/1997 | Hammerslag |
| 5,674,231 A | 10/1997 | Green et al. |
| 5,676,689 A | 10/1997 | Kensey et al. |
| 5,681,334 A | 10/1997 | Evans et al. |
| 5,700,277 A | 12/1997 | Nash et al. |
| 5,725,498 A | 3/1998 | Janzen et al. |
| 5,725,551 A | 3/1998 | Myers et al. |
| 5,728,122 A | 3/1998 | Leschinsky et al. |
| 5,728,132 A | 3/1998 | Van Tassel et al. |
| 5,728,133 A | 3/1998 | Kontos |
| 5,728,134 A | 3/1998 | Barak |
| 5,741,223 A | 4/1998 | Janzen et al. |
| 5,746,755 A | 5/1998 | Wood et al. |
| 5,755,727 A | 5/1998 | Kontos |
| 5,759,194 A | 6/1998 | Hammerslag |
| 5,766,183 A | 6/1998 | Sauer |
| 5,766,206 A | 6/1998 | Wijkamp et al. |
| 5,779,719 A | 7/1998 | Klein et al. |
| 5,782,861 A | 7/1998 | Cragg et al. |
| 5,792,173 A | 8/1998 | Breen et al. |
| 5,810,810 A | 9/1998 | Tay et al. |
| 5,810,846 A | 9/1998 | Virnich et al. |
| 5,810,884 A | 9/1998 | Kim |
| 5,814,065 A | 9/1998 | Diaz |
| 5,820,631 A | 10/1998 | Nobles |
| 5,827,299 A | 10/1998 | Thomason et al. |
| 5,830,130 A | 11/1998 | Janzen et al. |
| 5,843,124 A | 12/1998 | Hammerslag |
| 5,853,421 A | 12/1998 | Leschinsky et al. |
| 5,855,559 A | 1/1999 | Van Tassel et al. |
| 5,855,585 A | 1/1999 | Kontos |
| 5,860,990 A | 1/1999 | Nobles et al. |
| 5,860,991 A | 1/1999 | Klein et al. |
| 5,861,004 A | 1/1999 | Kensey et al. |
| 5,861,005 A | 1/1999 | Kontos |
| 5,868,762 A | 2/1999 | Cragg et al. |
| 5,876,411 A | 3/1999 | Kontos |
| 5,902,311 A | 5/1999 | Andreas et al. |
| 5,906,631 A | 5/1999 | Imran |
| 5,910,155 A | 6/1999 | Ratcliff et al. |
| 5,919,207 A | 7/1999 | Taheri |
| 5,941,897 A | 8/1999 | Myers |
| 5,957,952 A | 9/1999 | Gershony et al. |
| 5,964,782 A | 10/1999 | Lafontaine et al. |
| 5,976,161 A | 11/1999 | Kirsch et al. |
| 5,980,539 A | 11/1999 | Kontos |
| 5,997,555 A | 12/1999 | Kontos |
| 6,007,562 A | 12/1999 | Harren et al. |
| 6,007,563 A | 12/1999 | Nash et al. |
| 6,017,359 A | 1/2000 | Gershony et al. |
| 6,024,747 A | 2/2000 | Kontos |
| 6,033,401 A | 3/2000 | Edwards et al. |
| 6,033,427 A | 3/2000 | Lee |
| 6,036,721 A | 3/2000 | Harren et al. |
| 6,042,601 A | 3/2000 | Smith |
| 6,045,569 A | 4/2000 | Kensey et al. |
| 6,048,357 A | 4/2000 | Kontos |
| 6,048,358 A | 4/2000 | Barak |
| 6,063,085 A | 5/2000 | Tay et al. |
| 6,071,300 A | 6/2000 | Brenneman et al. |
| 6,077,279 A | 6/2000 | Kontos |
| 6,090,130 A | 7/2000 | Nash et al. |
| 6,110,184 A | 8/2000 | Weadock |
| 6,120,524 A | 9/2000 | Taheri |
| 6,126,675 A | 10/2000 | Shchervinsky et al. |
| 6,136,010 A | 10/2000 | Modesitt et al. |
| 6,139,556 A | 10/2000 | Kontos |
| 6,162,192 A | 12/2000 | Cragg et al. |
| 6,174,322 B1 | 1/2001 | Schneidt |
| 6,179,863 B1 | 1/2001 | Kensey et al. |
| 6,183,496 B1 | 2/2001 | Urbanski |
| 6,193,670 B1 | 2/2001 | Van Tassel et al. |
| 6,197,042 B1 | 3/2001 | Ginn et al. |
| 6,206,893 B1 | 3/2001 | Klein et al. |
| 6,206,895 B1 | 3/2001 | Levinson |
| 6,231,561 B1 | 5/2001 | Frazier et al. |
| 6,245,080 B1 | 6/2001 | Levinson |
| 6,398,796 B2 | 6/2002 | Levinson |
| 6,425,911 B1 | 7/2002 | Akerfeldt et al. |
| 6,425,924 B1 | 7/2002 | Rousseau |
| 6,508,828 B1 | 1/2003 | Akerfeldt et al. |
| 6,547,806 B1 | 4/2003 | Ding |
| 6,569,185 B2 | 5/2003 | Ungs |
| 6,596,012 B2 | 7/2003 | Akerfeldt et al. |
| 6,596,014 B2 | 7/2003 | Levinson et al. |
| 6,682,489 B2 | 1/2004 | Tenerz et al. |
| 6,712,837 B2 | 3/2004 | Akerfeldt et al. |
| 6,860,895 B1 * | 3/2005 | Akerfeldt et al. ............ 606/215 |
| 6,929,655 B2 * | 8/2005 | Egnelov et al. ............ 606/213 |
| 2002/0010418 A1 * | 1/2002 | Lary et al. ............ 604/101.04 |
| 2003/0060846 A1 | 3/2003 | Egnelov et al. |
| 2005/0085851 A1 * | 4/2005 | Fiehler et al. ............ 606/213 |
| 2005/0107826 A1 | 5/2005 | Zhu et al. |
| 2005/0149117 A1 | 7/2005 | Khosravi et al. |
| 2005/0228443 A1 | 10/2005 | Yassinzadeh |

* cited by examiner

TISSUE PUNCTURE CLOSURE DEVICE WITH SCROLL GEAR TRANSMISSION TAMPING SYSTEM

FIELD OF THE INVENTION

This invention relates generally to medical devices and more particularly to devices for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,179,863; 6,090,130; and 6,045,569 and related patents that are hereby incorporated by reference.

Typical closure devices such as the ones described in the above-mentioned patents place a sealing plug at the tissue puncture site. Successful deployment of the sealing plug, however, requires that it be manually ejected from within a device sheath and tamped down to an outer surface of the tissue puncture using a tamping tube. The tamping procedure cannot commence until the device sheath (within which the tamping tube is located) has been removed so as to expose the tamping tube for manual grasping. Under certain conditions, removal of the sheath prior to tamping the sealing plug may cause the sealing plug itself to be retracted from the tissue puncture, hindering subsequent placement of the sealing plug, and resulting in only a partial seal and associated late bleeding from the tissue puncture. Accordingly, there is a need for improving the mechanism for deployment of the sealing plug at the site of a tissue puncture.

SUMMARY

The present invention meets the above-described needs and others. Specifically, the present invention provides methods and systems for closing internal tissue punctures. However, unlike prior systems, the present invention provides automatic tamping to a sealing plug as the closure device is retracted. In addition, the present invention allows the automatic tamping system to change gear ratio when, for example, the sealing plug passes through a small tip or other outlet.

In one of many possible embodiments, the present invention provides a tissue puncture closure device for partial insertion into and sealing of an internal tissue wall puncture. The device comprises a filament extending from a first end of the closure device to a second end of the closure device, an anchor for insertion through the tissue wall puncture attached to the filament at the second end of the closure device, a sealing plug slidingly attached to the filament adjacent the anchor, and a tamping assembly comprising a tamping device and a variable gear ratio transmission. The tamping device may comprise a tamping tube operatively connected to the variable gear ratio transmission. The variable gear ratio transmission is activated automatically upon retraction of the tissue puncture closure device from the puncture. The variable gear ratio transmission may comprise at least two scroll gears.

According to some embodiments, the variable gear ratio transmission comprises a first scroll gear having a continuously changing radius, and a second scroll gear meshed with the first scroll gear. The second scroll gear also has a continuously changing radius matching the first scroll gear.

According to some embodiments, the variable gear ratio transmission comprises a first scroll gear having a first radius along a first radial degree segment and a second radius along a second radial degree segment, and a second scroll gear meshed with the first scroll gear, the second scroll gear also having a first radius along a first radial degree segment and a second radius along a second radial degree segment.

According to some embodiments, the variable gear ratio transmission comprises a first scroll gear having a first continuously variable radius along a first radial degree segment, and a second constant radius along a second radial degree segment and a second scroll gear meshed with the first scroll gear, the second scroll gear also having a first continuously variable radius along a first radial degree segment and a second radius along a second radial degree segment.

According to some embodiments, the variable gear ratio transmission comprises a first gear having a discontinuity where a gear radius changes abruptly, and a second gear meshed with the first gear having a mating discontinuity.

According to some embodiments, the variable gear ratio transmission comprises a first scroll gear mounted on a first axis, a spool mounted on the first axis and connected to the first scroll gear, a portion of the filament wound on the spool, a second scroll gear mounted on a second axis meshed with the first scroll gear, and an output gear mounted on the second axis and connected to the second scroll gear. The tamping device may comprise a tamping tube meshed with the output gear.

According to some embodiments, the tamping device comprises a tamping tube, and the tamping tube is driven by the variable gear ratio transmission to tamp the sealing plug. The variable gear ratio transmission may comprise a transducer for effecting a distal force on the sealing plug upon withdrawal of the closure device from the tissue wall puncture. The variable gear ratio transmission may include a scroll gearset comprising first and second scroll gears, a spool with a portion of the filament wound thereon connected to the first scroll gear, and an output gear connected to a second scroll gear and meshed with the tamping device. The spool rotates and drives the first scroll gear in a first direction, and the output gear drives the tamping device in a second direction, when the anchor is deployed and the closure device is retracted from the tissue wall puncture. The scroll gears may be engaged initially in a low gear ratio, the scroll gears increasing in gear ratio as they rotate via an increasing circumference of the output scroll gear and a decreasing circumference of the input scroll gear.

Another aspect of the invention provides a tissue puncture closure device for partial insertion into and sealing of a tissue puncture in an internal tissue wall accessible through a percutaneous incision. The device comprises an anchor for disposition on a distal side of the internal tissue wall, a sealing plug for disposition on a proximal side of the internal tissue wall, a filament connected between the anchor and the sealing plug, and a scroll gear transmission for automatically tamping the sealing plug along the filament distally towards the anchor. The closure device may further comprise a tamping device operatively connected to the scroll gear transmission. The scroll gear transmission may comprise a storage spool onto which a proximal end of the filament is wound, a first scroll gear connected to the storage spool, and a second scroll gear meshed with the first scroll gear. The scroll gear transmission may include a first scroll gear having a gradually changing radius, a second scroll gear meshed with the first scroll gear, the second scroll gear also having a gradually changing radius. Alternatively, the first and second scroll gears may have a sudden change in radius.

According to some embodiments, the tamping device is operatively connected to the scroll gear transmission, and the scroll gear transmission comprises a storage spool onto which a proximal end of the filament is wound, and a scroll gearset driven by the storage spool, such that withdrawal of the closure device from the tissue puncture with the anchor bearing against the internal tissue wall unwinds the filament from the storage spool and actuates the scroll gearset. The storage spool may drive the scroll gearset, and the scroll gearset directly or indirectly provides a tamping force to the tamping device.

Another aspect of the invention provides a method of sealing a tissue puncture in an internal tissue wall accessible through a percutaneous incision. The method comprises withdrawing a closure device from the tissue puncture and automatically transducing a motive force generated by withdrawal of the closure device in a first direction to a tamping force in a second direction using scroll gears. The method may include automatically continuously changing a gear ratio of the scroll gears as they rotate. The continuously changing gear ratio may be an increasing gear ratio. Alternatively, the method may comprise abruptly changing the radius the scroll gears as they rotate, a first of the scroll gears abruptly changing from a first radius to a second radius at least 1.5 times larger than the first radius, and simultaneously changing a second of the scroll gears from a first radius to a second radius at least 1.5 times smaller than the first radius of the second scroll gear.

Another aspect of the invention provides another method of sealing a tissue puncture in an internal tissue wall accessible through a percutaneous incision. The method comprises providing a tissue puncture closure device having a carrier tube, a filament extending through the carrier tube to an anchor and to a sealing plug located proximal of the anchor for disposition and anchoring about the tissue puncture, the tissue puncture closure device also comprising a tamping assembly comprising a tamping device and a variable gear ratio transmission; inserting the tissue puncture closure device into the percutaneous incision, deploying the anchor in the tissue puncture, at least partially withdrawing the closure device from the percutaneous incision, forcing the sealing plug through an outlet of the carrier tube, and automatically changing a gear ratio of the variable gear ratio transmission after the sealing plug is forced through the outlet of the carrier tube. The automatically changing a gear ratio may comprise providing a scroll gearset of variable radius gears. Automatically changing gear ratio may comprise unwinding a filament from a spool of the tamping assembly by the withdrawing of the closure device, and driving a scroll gearset with the spool. The tamping device may be driven by the scroll gearset.

Another aspect of the invention provides a tissue puncture closure device for partial insertion into and sealing of an internal tissue wall puncture. The closure device includes a filament extending from a first end of the closure device to a second end of the closure device, an anchor for insertion through the tissue wall puncture attached to the filament at the second end of the closure device, a sealing plug slidingly attached to the filament adjacent to the anchor, a tamping device adjacent to the sealing plug, and an automatic, multi-speed scroll transmission driven by the filament and operatively connected to the tamping device for advancing the tamping device toward the sealing plug.

Additional advantages and novel features of the invention will be set forth in the description which follows or may be learned by those skilled in the art through reading these materials or practicing the invention. The advantages of the invention may be achieved through the means recited in the attached claims.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

As mentioned above, vascular procedures are conducted throughout the world and require access to an artery through a puncture. Most often, the artery is a femoral artery. To close the puncture following completion of the procedure, many times a closure device is used to sandwich the puncture between an anchor and a sealing plug. However, sometimes the sealing plug is not properly seated against an exterior situs of the arteriotomy. If the plug does not seat against the arteriotomy, there is a potential for elongated bleeding. The present invention describes methods and apparatus to reduce or eliminate movement or misplacement of the sealing plug with a compact device. While the vascular instruments shown and described below include insertion sheaths and puncture sealing devices, the application of principles described herein are not limited to the specific devices shown. The principles described herein may be used with any vascular closure device. Therefore, while the description below is directed primarily to arterial procedures and certain embodiments of a vascular closure device, the methods and apparatus are only limited by the appended claims.

As used in this specification and the appended claims, the term "tamp" or "tamping" is used broadly to mean packing down by one or a succession of blows or taps or smooth, steady pressure, but not by excessive force. A "tamping tube" is used broadly to mean any elongated device or series of devices, including any intermediate components, used alone or in combination to tamp something else directly or indirectly. "Engage" and "engageable" are also used broadly to mean interlock, mesh, or contact between two devices. "Mesh" means to interlock or contact. A "spool" is a cylinder or other device on which something else is at least partially wound. A "lumen" refers to any open space or cavity in a bodily organ or device, especially in a blood vessel. "Automatic" means no action or intervention is required by a human operator. "Transduce" means to convert a force or other input energy in one form into output energy or forces of another form or direction. "Scroll gears" refer to gears with or without teeth that have a discontinuity, or a variation or change in radius. "Gradually" means advancing or progressing by regular or continuous degrees, or absent any abrupt changes. "Sudden" refers to a rapid, abrupt, or quick change. The words "including" and "having," as used in the specification, including the claims, have the same meaning as the word "comprising."

Referring now to the drawings, and in particular to FIGS. 1-4, a vascular puncture closure device 100 is shown according to the prior art. The vascular puncture closure device 100 includes a carrier tube 102 with a filament or suture 104 extending at least partially therethrough. The closure device 100 also includes a first or proximal end 106 and a second or distal end 107. External to a second or distal end 107 of the carrier tube 102 is an anchor 108. The anchor is an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may be comprised of randomly oriented fibrous material bound together by chemical means. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the closure device 100 is properly placed and the anchor 108 deployed (see FIG. 4).

Figure 1:
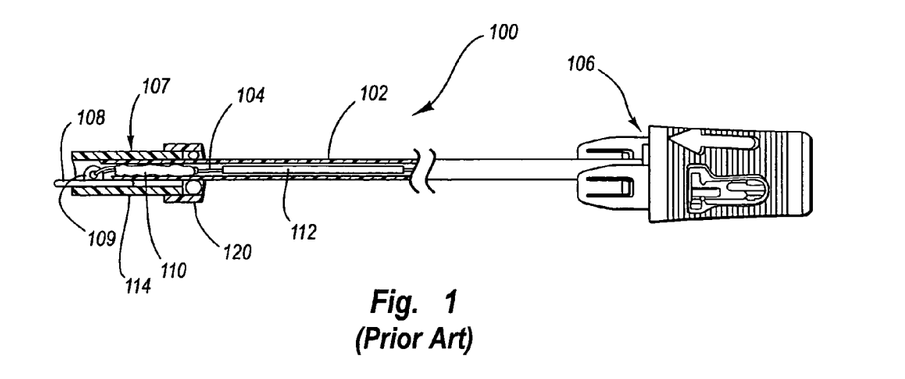
FIG. 1 is a partial cut-away view of a tissue closure device according to the prior art.

The carrier tube 102 typically includes a tamping tube 112 disposed therein. The tamping tube 112 is slidingly mounted on the suture 104 and may be used by an operator to tamp the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 2:
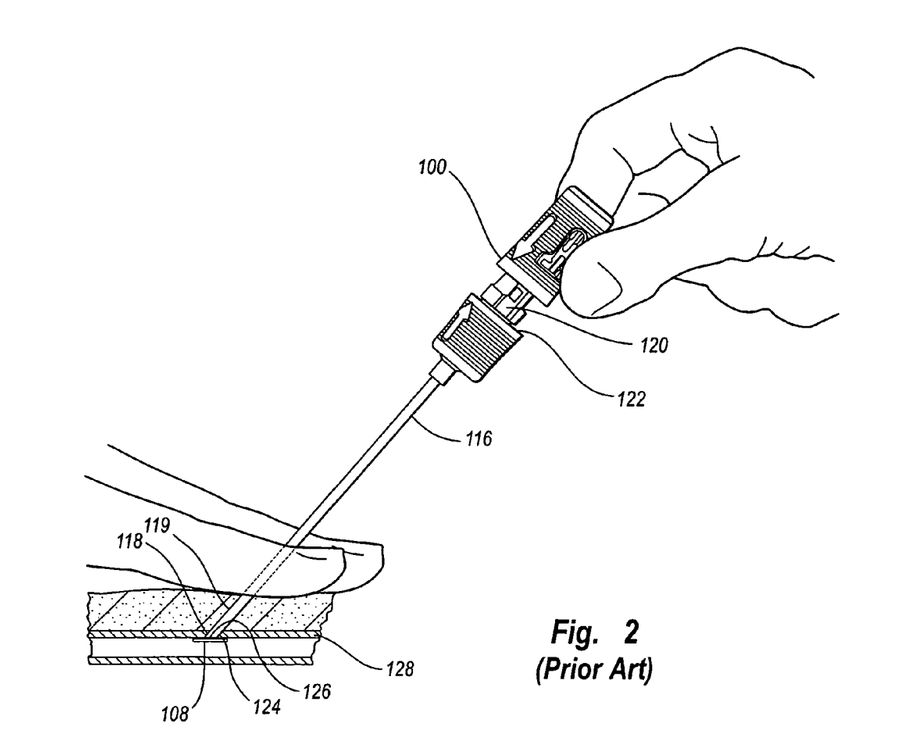
FIG. 2 is a side view of the tissue closure device of FIG. 1 engaged with an artery according to the prior art.
Figure 3:
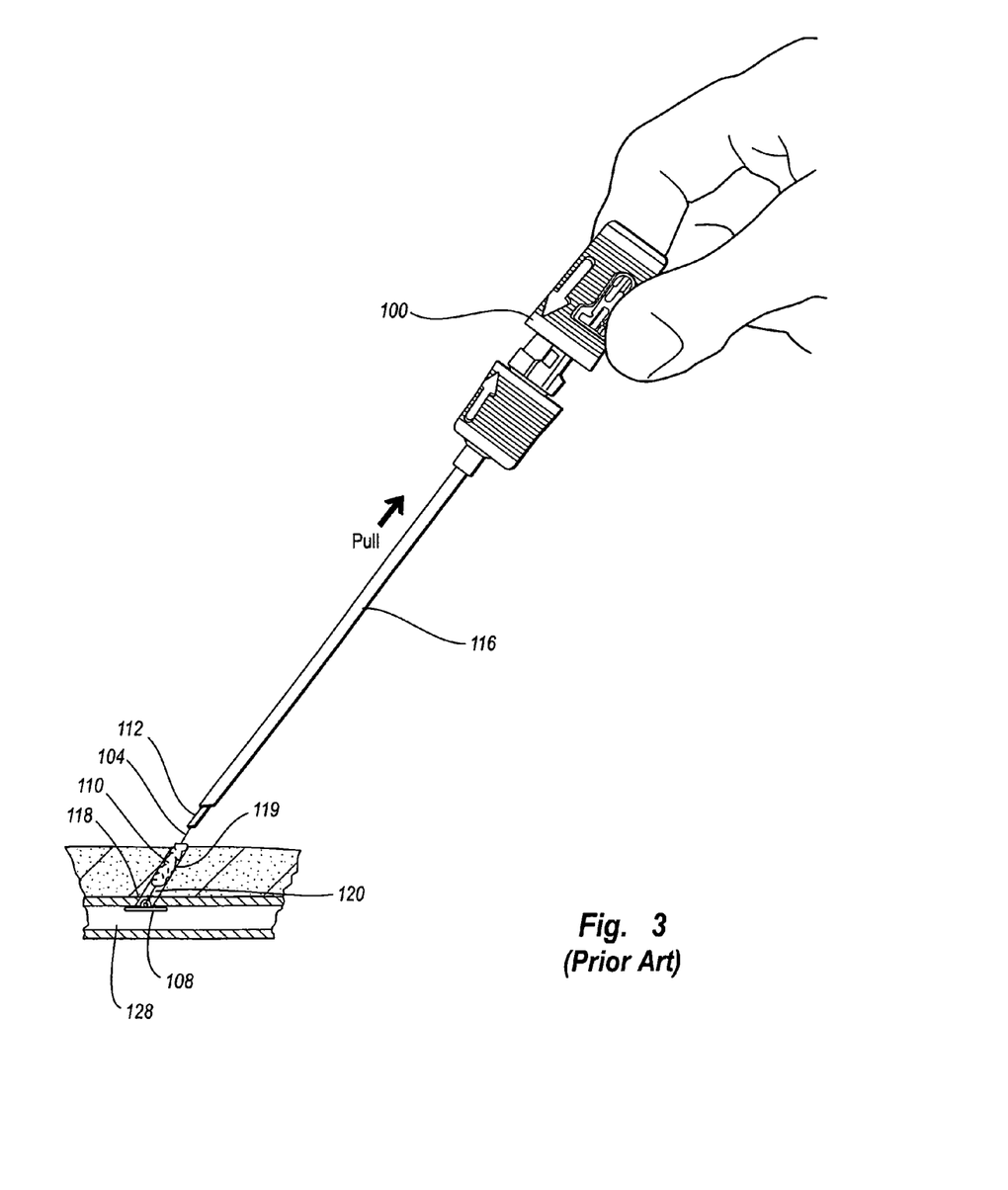
FIG. 3 is a side view of the tissue closure device of FIG. 1 being withdrawn from an artery according to the prior art to deploy a collagen sponge.
Figure 4:
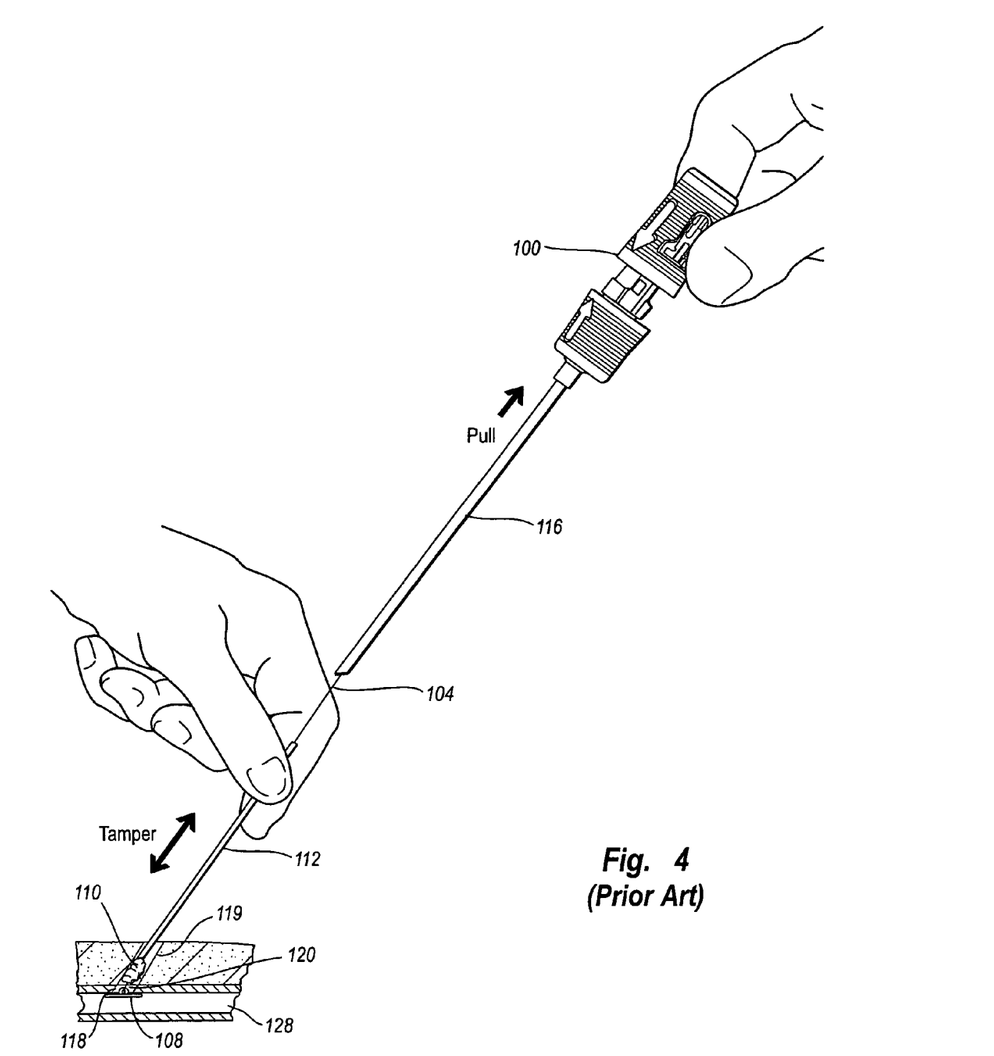
FIG. 4 is a side view of the tissue closure device of FIG. 1 illustrating tamping of the collagen sponge according to the prior art.

The flush arrangement of the anchor 108 and carrier tube 102 allows the anchor 108 to be inserted into an insertion sheath 116 as shown in FIGS. 2-4, and eventually through an arterial puncture 118. The insertion sheath 116 is shown in FIGS. 2-4 inserted through a percutaneous incision 119 and into an artery 128. However, the bypass tube 114 (FIG. 1) includes an oversized head 120 that prevents the bypass tube 114 from passing through an internal passage of the insertion sheath 116. Therefore, as the puncture closure device 100 is inserted into the insertion sheath 116, the oversized head 120 bears against a surface 122 of the insertion sheath 116. Further insertion of the puncture closure device 100 results in sliding movement between the carrier tube 102 (FIG. 1) and the bypass tube 114, releasing the anchor 108 from the bypass tube 114 (FIG. 1). However, the anchor 108 remains in the flush arrangement shown in FIG. 1 following release from the bypass tube 114 as the insertion sheath 116 continues to limit anchor 108 movement.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 thereof. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the puncture closure device 100 and the insertion sheath 116 are withdrawn together, forcing the collagen pad 110 through the tip of the carrier tube 102 and depositing it in the incision tract 119. The tamping tube 112 is also exposed. With the tamping tube 112 fully exposed as shown in FIG. 4, the collagen pad 110 is manually tamped, and the anchor 108 and collagen pad 110 are cinched together and held in place with the self-tightening slip-knot on the suture 102. Thus, the tissue puncture is sandwiched between the anchor 108 and the collagen pad 110, thereby sealing the tissue puncture 118. The suture 104 is then cut and the incision tract 119 may be closed. The suture 104, anchor 108, and collagen pad 110 are generally made of resorbable materials and therefore remain in place while the puncture 118 heals.

Using the typical tissue puncture closure device 100 described above, however, the tamping of the collagen pad 110 cannot commence until the sheath 116 has been removed so as to expose the tamping tube 112 for manual grasping. Under certain conditions, removal of the sheath 116 prior to tamping the collagen pad 110 causes the collagen pad 110 to retract from the tissue puncture 118, creating a gap 120 between the collagen pad 110 and the puncture 118. The gap 120 may remain even after tamping as shown in FIG. 4, and sometimes results in only a partial seal and bleeding from the tissue puncture 118.

Therefore, the present specification describes a tissue puncture closure device that automatically drives a sealing plug toward a tissue puncture upon withdrawal of the tissue puncture closure device from the tissue puncture site. The mechanism for automatically driving the sealing plug also includes a transmission with a variable gear ratio. While the preferred embodiments of the tissue puncture closure device are shown and described below, the principles of the present specification may be incorporated into any of a number of tissue puncture closure devices. The specific embodiments described below are for illustrative purposes only, and are not limiting.

As described above, the general structure and function of tissue puncture closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Figure 5:
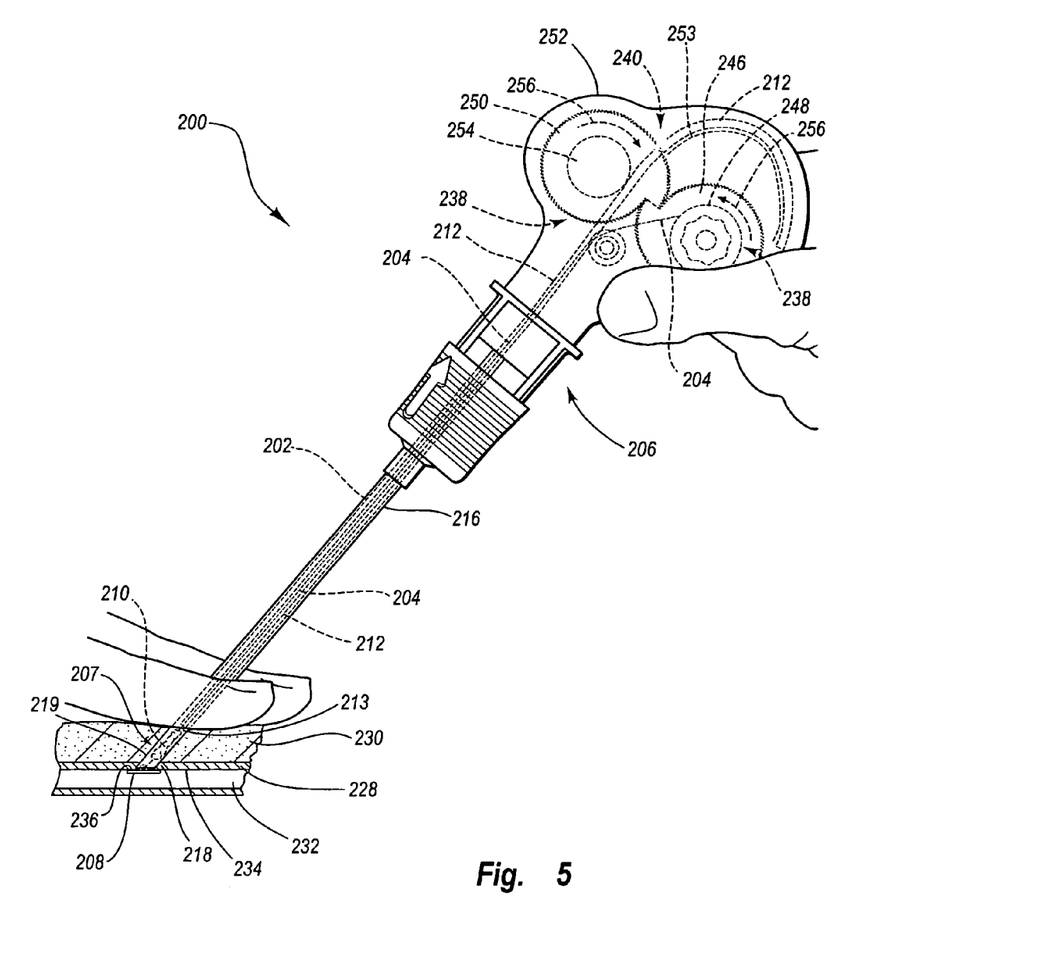
FIG. 5 is a side view of a tissue closure device with a scroll gear transmission for automatic tamping according to one embodiment of the present invention.

Referring now to FIG. 5, a tissue puncture closure device 200 is shown according to one embodiment of the present invention. The closure device 200 has particular utility when used in connection with intravascular procedures, such as angiographic dye injection, cardiac catheterization, balloon angioplasty and other types of recanalizing of atherosclerotic arteries, etc. as the closure device 200 is designed to cause immediate hemostasis of the blood vessel (e.g., arterial) puncture. However, it will be understood that while the description of the preferred embodiments below are directed to the sealing off of percutaneous punctures in arteries, such devices have much more wide-spread applications and can be used for sealing punctures or incisions in other types of tissue walls as well. Thus, the sealing of a percutaneous puncture in an artery, shown herein, is merely illustrative of one particular use of the tissue closure device 200 of the present invention.

The tissue closure device 200 includes a first or proximal end 206 and a second or distal end 207. A carrier tube 202 extends from the proximal end 206 to the distal end 207 and includes an outlet 213 at the distal end 207. The carrier tube 202 may be made of plastic or other material and is designed for insertion through a sheath 216, which is designed for insertion through a percutaneous incision 219 in a tissue layer 230 and into a lumen 232. According to FIG. 5, the lumen 232 comprises an interior portion of a femoral artery 228.

At the distal end 207 of the carrier tube 202 there is an anchor 208 and a sealing plug 210. The anchor 208 of the present embodiment is an elongated, stiff, low-profile member arranged to be seated inside the artery 228 against an artery wall 234 contiguous with a puncture 218. The anchor 208 is preferably made of a biologically resorbable polymer. The sealing plug 210 is formed of a compressible sponge, foam, or fibrous mat made of a non-hemostatic biologically resorbable material such as collagen, and may be configured in any shape so as to facilitate sealing the tissue puncture 218.

The sealing plug 210 and anchor 208 are connected to one another by a filament or suture 204 that is also biologically resorbable. The anchor 208, the sealing plug 210, and the suture 204 are collectively referred to as the "closure elements" below. As shown in FIG. 5, the anchor 208 is arranged adjacent to and exterior of the distal end 207 of the sheath 216, while the sealing plug 210 is initially disposed within the carrier tube 202. Although the anchor 208 is shown deployed with a first surface 236 abutting the artery wall 234, it will be understood that initially the anchor is arranged axially along the carrier tube 202 to facilitate insertion into the lumen 232 (see, for example, the anchor 108 of FIG. 1). The suture 204 extends distally from the first end 206 of the closure device 200 through the carrier tube 202. The suture 204 may be threaded through one or more perforations in the sealing plug 210, through a hole in the anchor 208, and proximally back toward the carrier tube 202 to the sealing plug 210. The suture 204 is preferably threaded again through a perforation or series of perforations in the sealing plug 210. The suture 204 may also be threaded around itself to form a self-tightening slip-knot. The suture 204 may thus connect the anchor 208 and the sealing plug 210 in a pulley-like arrangement to cinch the anchor 208 and the sealing plug 210 together when the carrier tube 202 is pulled away from the anchor 208 and the sealing plug 210, sandwiching and locking the anchor 208 and plug 210 together and thereby sealing the tissue puncture 218.

The carrier tube 202 houses a tamping device, such as a tamping tube 212, for advancing the sealing plug 210 along the suture 204 and against the anchor 208. The tamping tube 212 is shown located partially within the carrier tube 202 and proximal of the sealing plug 208. The tamping tube 212 is preferably an elongated tubular member that may be rigid or flexible and formed of any suitable material. For example, according to one embodiment, the tamping tube 212 is made of polyurethane. The tamping tube 212 shown in FIG. 5 is flexible and extends into a housing or handle 252. The tamping tube 212 may curve around a guide 253 in the handle 252 as shown in FIG. 5. Alternatively, the handle 252 may be elongated proximally, allowing the tamping tube 212 to extend into the elongated handle without bending. The suture 204 extends through the tamping tube 212 from the first end 206 to the second end 207, but is not directly connected thereto. Accordingly, the suture 204 and tamping tube 212 are free to slide past one another.

According to the embodiment of FIG. 5, the suture 204 diverges from the tamping tube 212 at the first end 206 and attaches to a component of a tamping assembly 238. The tamping tube 212 may thus include an open trough 251 (FIG. 6) allowing the suture 204 to exit. The tamping assembly 238 may include the tamping tube 212, which extends into the carrier tube 202, but the remainder of the tamping assembly 238 is located within the handle 252 of the closure device 200. Embodiments of the automatic tamping assembly 238 are described in more detail below with reference to FIGS. 6 and 7.

The tamping tube 212 automatically pushes the sealing plug 210 through the outlet 213 of the carrier tube 202 upon retraction of the closure device 200 from the incision 219, if the anchor 208 is deployed within the artery 228 as shown in FIG. 5. The tamping tube 212 or other tamping device may comprise a rack receptive of gear teeth (shown in FIGS. 6 and 7). Alternatively, the tamping tube 212 may align with and abut a separate tamping driver rack, and the separate tamping driver rack would then advance the tamping tube 212.

In practice, the carrier tube 202 of the closure device 200 (containing the closure elements described above) is inserted into the insertion sheath 216, which is already inserted within the artery 228. As the closure device 200 and the associated closure elements are inserted into the insertion sheath 216, the anchor 208 passes through and out of the distal end of the insertion sheath 216 and is inserted into the artery lumen 232. As mentioned above, the anchor 208 is initially arranged substantially parallel with the carrier tube 202 to facilitate insertion of the anchor 208 through the percutaneous incision 219 and into the lumen 232.

The closure device 200 is then withdrawn from the insertion sheath 216 until the anchor 208 catches on the distal end of the insertion sheath 216 and rotates to the position shown in FIG. 5. When resistance to further retraction of the closure device 200 is felt by an operator, the closure device 200 and the insertion sheath 216 are withdrawn together, causing the anchor 208 to anchor itself within the artery 228 against the artery wall 234. With the anchor 208 anchored within the artery 228 at the puncture site 218, further retraction of the closure device 200 and insertion sheath 216 forces the sealing plug 210, which is attached to the suture 204, out through the outlet 213 of the carrier tube 202.

However, unlike previous closure devices that require a separate, manual tamping procedure to properly deposit the sealing plug 210, the closure device 200 of the present invention automatically forces the sealing plug 210 out of the carrier tube 202 and tamps it toward the anchor 208 in a continuous movement as the handle 252 is retracted. Therefore, the sealing plug 210 is tamped toward the anchor by the automatic tamping assembly 238 while the carrier tube 202 is still arranged adjacent to the puncture 218 in the femoral artery 228, reducing or eliminating any gaps that may otherwise occur between the sealing plug 210 and the puncture 218 in the femoral artery 228.

In addition, by placing tension on or pulling the suture 204 away from the puncture tract 219, the suture 204 may cinch and lock (with a slip knot or the like) together the anchor 208 and the sealing plug 210, sandwiching the artery wall 234 between the anchor 208 and the sealing plug 210. The force exerted by the tamping tube 212 toward the anchor 203 and the cinching together of the anchor 208 and sealing plug 210 by the filament 204, also causes the sealing plug 210 to deform radially outward within the puncture tract 219 and function as an anchor on the proximal side of the tissue puncture site 218.

As the sealing plug 210 is pushed through the outlet 213 of the carrier tube 202, a variable force and various amounts torque from the automatic tamping assembly 238 may be required. Therefore, the automatic tamping assembly 238 includes an automatic transmission with a variable gear ratio to facilitate easy advancement of the sealing plug 210 out of the carrier tube 202 and toward the anchor 208. The automatic transmission with a variable gear ratio provides for increased torque as the sealing plug 210 is forced out of the outlet 213, and a greater speed or a greater gear ratio once the sealing plug 210 has cleared the outlet 213 to fully tamp it toward the anchor 208.

Figure 6:
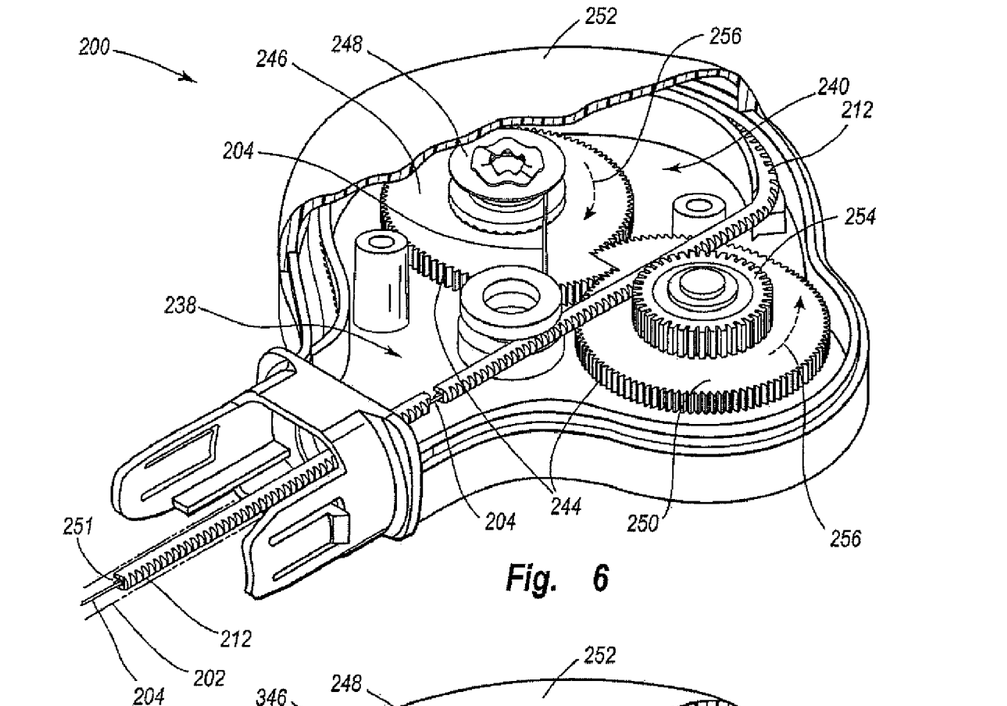
FIG. 6 is a partial assembly view of one embodiment of the scroll gear transmission of FIG. 5 according to the present invention.

Automatic driving of the tamping tube 212 toward the sealing plug 210 and/or cinching the plug and the anchor 208 may be facilitated by any of a number of mechanisms. For example, one automatic variable gear ratio transmission 240 that may be disposed in the housing 252 of the closure device 200 is shown in FIG. 6. The automatic gear ratio changing transmission 240 is part of the automatic tamping assembly 238. The automatic gear ratio changing transmission 240 may comprise at least two speeds.

According to the embodiment of FIG. 6, retraction of the closure device 200 from the tissue puncture site 218 (FIG. 5) automatically effects tamping of the sealing plug 210 (FIG. 5). The retraction or motive force in a first direction is automatically transduced, according to FIG. 6, by the automatic tamping assembly 238 to a tamping force in a second direction. The details of transducing the retraction force to a tamping force are described below.

According to the automatic tamping assembly 238 of FIG. 6, the gear ratio changing transmission 240 includes a scroll gearset 244. The scroll gearset 244 comprises a first scroll gear 246, and a second scroll gear 250 engaged or meshed with the first scroll gear 246. The scroll gearset 244 is driven by a spool 248 coupled to or engaged with the scroll gearset 244. According to the embodiment of FIG. 6, the suture 204 is partially wound about the spool 248, and the spool 248 is coaxially attached to the first scroll gear 246. Because the spool 248 is attached coaxially to the first scroll gear 246, they rotate together at the same angular velocity. However, there may be a torque limiting clutch between the first scroll gear 246 and the spool 248, such as mating fan surfaces biased together by a spring.

Withdrawal of the closure device 200 (FIG. 5) from the tissue puncture site 218 (if the anchor 208 (FIG. 5) is deployed) causes the suture 204 to unwind from the spool 248. The spool 248 rotates as the suture 204 unwinds and provides a torsional motive force that may be transduced to a linear tamping force.

According to the embodiment of FIG. 6, the torsional motive force provided by the unwinding spool 248 is transduced into the linear tamping by the scroll gearset 244. An output gear 254 is attached coaxially to the second scroll gear 250. Therefore, the output gear 254 rotates with the second scroll gear 250. The output gear 254 is engaged with the tamping tube 212. The tamping tube 212 moves linearly as the output gear 254 rotates. The output gear 254 is preferably a conventional circular gear with a constant radius.

However, the first and second scroll gears 246, 250 have variable radii. According to the embodiment of FIG. 6, each of the first and second scroll gears 246, 250 exhibit continuously changing radii with a discontinuity. Therefore, the first and second scroll gears 246, 250 have mating circumferences that provide a continuously changing gear ratio. As shown in FIG. 6, the first and second scroll gears 246, 250 will exhibit an increasing gear ratio as the scroll gears rotate in the direction of arrows 256. The gear ratio may begin at a gear ratio of less than 1:1 as shown in FIG. 6, and may increase as the scroll gears 246, 250 rotate to a ratio of 1.5:1 to 5:1 or more. The gear ratio of the scroll gearset 244 shown in FIG. 6 gradually increases as the scroll gears 246, 250 rotate.

Figure 7:
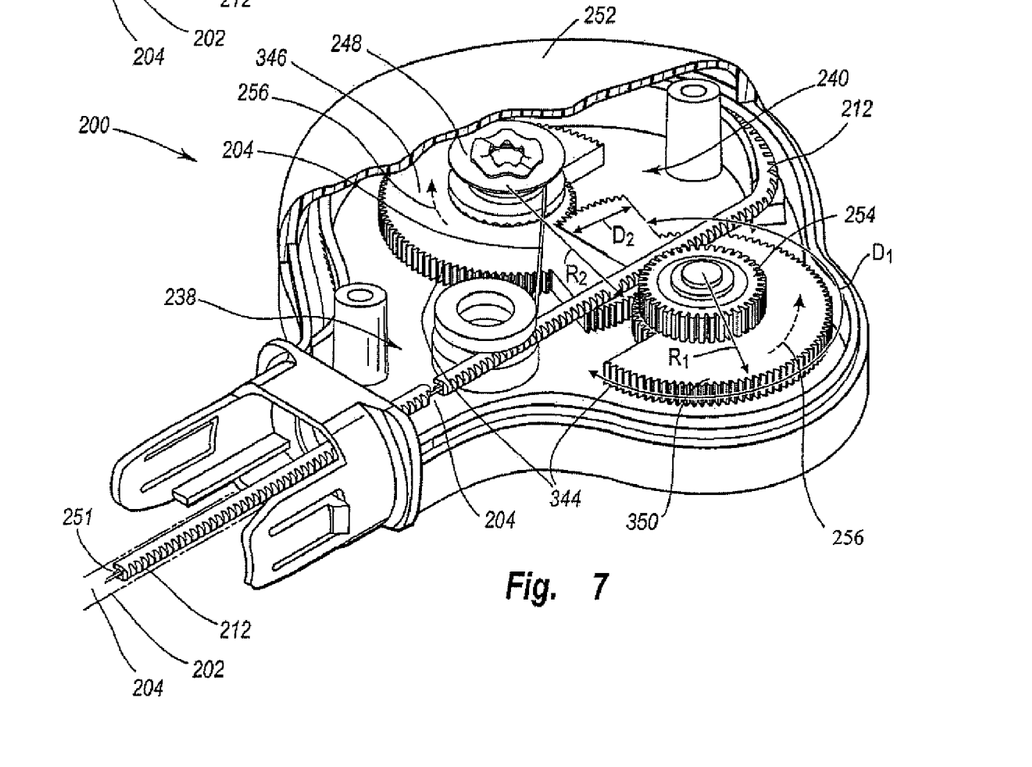
FIG. 7 is a partial assembly view of another embodiment of the scroll gear transmission of FIG. 5 according to the present invention.
Figure 8:
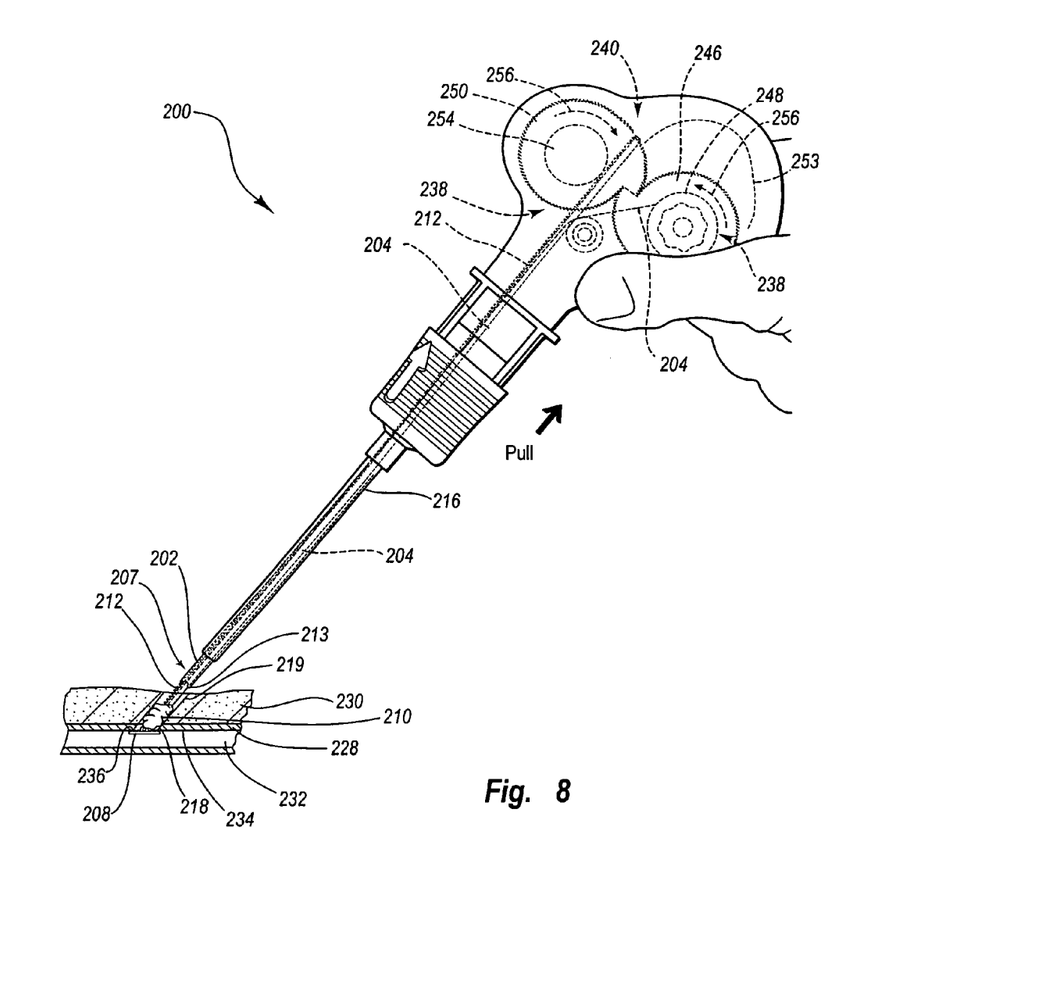
FIG. 8 is a side view of the tissue closure device of FIG. 5 with a sealing plug fully tamped according to one embodiment of the present invention.

The scroll gearset 244 may exhibit other variable radii arrangements as well. For example, as shown in FIG. 7, a scroll gearset 344 may include first and second scroll gears 346, 350 that exhibit sudden changes in radius, and thus sudden changes in gear ratio. The first and second scroll gears 346, 350 have a first radius R1 that may be variable, continuously variable, or constant along a first radial degree segment D1, and a second radius R2 that may be substantially larger (and variable, continuously variable, or constant) than the first radius R1 along a second radial degree segment D2. The second radial degree segment D2 is preferably designed to be of sufficient length to ensure that upon rotation, the sealing plug 210 (FIG. 5) will be driven by the tamping tube 212 a sufficient distance to clear the carrier tube 202 before the first radial degree segments D1 engage. When the first radial degree segments D1 do engage, the gear ratio increases and moves the tamping tube 212 at a faster rate. The result of the tamping operation by rotation of the scroll gearset 244/344 is shown in FIG. 8, where the sealing plug 210 has been fully tamped.

There may be multiple sudden or gradual changes as well. The scroll gearsets 244, 344 shown in FIGS. 6-7 are only exemplary. Any scroll gearset is contemplated by the present invention to provide an automatically changing gear ratio.

Operation of the embodiment of FIGS. 5-8 is as follows. As the closure device 200 is retracted from the puncture tract 219 with the anchor 208 deployed, the suture 204, which is threaded through the anchor 208, unwinds from and causes rotation of the spool 248. The spool 248 drives the first scroll gear 246/346 as the spool 248 rotates via the coaxial connection therebetween. As the first scroll gear 246/346 rotates, it drives the second scroll gear 250/350. The coaxially mounted output gear 254 rotates with the second scroll gear 250/350. The output gear 254 meshes with the tamping tube 212, and the tamping tube 212 is driven distally to force the sealing plug 210 out of the carrier tube 202 and the insertion sheath 216. The gear ratio of the scroll gearset 244/344 is preferably less than 1:1 initially, to provide additional torque as the sealing plug 210 is forced through the outlet 213 of the carrier tube 202 and the sheath 216.

However, after the sealing plug 210 has cleared the carrier tube 202, the torque necessary to tamp the sealing plug 210 toward the anchor 208 decreases. Moreover, it may be desirable to increase the gear ratio to move the tamping tube 212 and tamp the sealing plug 210 at a faster rate. Increasing the gear ratio also reduces the stroke an operator must retract the closure device 200. Accordingly, the gear ratio is gradually or suddenly increased as the scroll gearset 244/344 rotates. Therefore, as the closing device 200 is retracted from the puncture tract 219, the sealing plug 210 is automatically forced out of the carrier tube 202 and tamped via the automatic variable gear ratio transmission 240 and the tamping tube 212. The sealing plug 210 is more likely to create a sufficient arterial seal without gaps between the sealing plug 210 and the anchor 208, as may otherwise occur with a separate manual tamping procedure. The suture 204 is ultimately cut, and the closure elements are left at the puncture site while the remainder of the closure device 200 is removed.

The preceding description has been presented only to illustrate and describe exemplary embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device for partial insertion into and sealing of an internal tissue wall puncture, comprising:
   a filament extending from a first end of the closure device to a second end of the closure device;
   an anchor for insertion through the tissue wall puncture attached to the filament at the second end of the closure device;
   a sealing plug slidingly attached to the filament adjacent to the anchor, the sealing plug configured to be compressed in an axial direction toward the anchor;
   a handle at the first end of the closure device, the handle comprising:
      a tamping assembly comprising a tamping device connected to a variable gear ratio transmission, wherein a first gear ratio of the variable gear ratio transmission is defined by engagement of a first portion of a first gear and a first portion of a second gear and is changeable to a second gear ratio defined by engagement of a second portion of the first gear with a second portion of the second gear when the sealing plug passes through an outlet of a carrier tube of the closure device, the second gear ratio providing distal advancement of the tamping device to compress the sealing plug in the axial direction.

2. A tissue puncture closure device for partial insertion into and sealing of an internal tissue wall puncture according to claim 1 wherein the tamping device comprises a tamping tube operatively connected to the variable gear ratio transmission.

3. A tissue puncture closure device for partial insertion into and sealing of an internal tissue wall puncture according to claim 1 wherein the variable gear ratio transmission is activated automatically upon retraction of the tissue puncture closure device from the puncture.

4. A tissue puncture closure device for partial insertion into and sealing of an internal tissue wall puncture according to claim 1, wherein the first gear and the second gear are scroll gears.

5. A tissue puncture closure device for partial insertion into and sealing of an internal tissue wall puncture according to claim 1, wherein
   the first gear has a continuously changing radius, and
   the second gear has a mating continuously changing radius.

6. A tissue puncture closure device for partial insertion into and sealing of an internal tissue wall puncture according to claim 1 wherein:
   the first gear has a first radius along a first radial degree segment, and a second radius along a second radial degree segment; and
   the second gear has a first radius along a first radial degree segment and a second radius along a second radial degree segment;
   the first and second radius of the first and second gears being defined from a rotational axis of each gear to a radially outer most point along a periphery of each gear.

7. A tissue puncture closure device for partial insertion into and sealing of an internal tissue wall puncture according to claim 1 wherein:
   the first gear has a first continuously variable radius along a first radial degree segment, and a second constant radius along a second radial degree segment; and
   the second gear has a first continuously variable radius along a first radial degree segment and a second constant radius along a second radial degree segment.

8. A tissue puncture closure device for partial insertion into and sealing of an internal tissue wall puncture according to claim 1 wherein:
   the first gear has a discontinuity wherein a gear radius changes abruptly; and
   the second gear has a mating discontinuity.

9. A tissue puncture closure device for partial insertion into and sealing of an internal tissue wall puncture according to claim 1 wherein the variable gear ratio transmission comprises:
   the first gear mounted on a first axis;
   a spool mounted on the first axis and connected to the first gear;
   a portion of the filament wound on the spool;
   the second gear mounted on a second axis;
   an output gear mounted on the second axis and connected to the second gear;
   wherein the tamping device comprises a tamping tube meshed with the output gear.

10. A tissue puncture closure device for partial insertion into and sealing of an internal tissue wall puncture according to claim 1 wherein the tamping device further comprises a tamping tube;
   wherein the tamping tube is driven by the variable gear ratio transmission to tamp the sealing plug;
   wherein the variable gear ratio transmission comprises a transducer for effecting a distal force on the sealing plug upon withdrawal of the closure device from the tissue wall puncture.

11. A tissue puncture closure device for partial insertion into and scaling of an internal tissue wall puncture according to claim 1 wherein the variable gear ratio transmission comprises:
   a spool with a portion of the filament wound thereon connected to the first gear;
   an output gear connected to the second gear and meshed with the tamping device;
   wherein the spool rotates and drives the first gear in a first direction, and the output gear drives the tamping device in a second direction, when the anchor is deployed and the closure device is retracted from the tissue wall puncture.

12. A tissue puncture closure device for partial insertion into and sealing of an internal tissue wall puncture according to claim 1, wherein the first and second gears engage initially at a first gear ratio and increase in gear ratio as they rotate.

13. A tissue puncture closure device for partial insertion into and sealing of an internal tissue wall puncture according to claim 1, wherein a gear ratio of the variable gear ratio transmission changes as the first gear and the second gear rotate.

14. A tissue puncture closure device for partial insertion into and sealing of an internal tissue wall puncture according to claim 1, wherein the second gear ratio is different than the first gear ratio.

15. A tissue puncture closure device for partial insertion into and sealing of a tissue puncture in an internal tissue wall accessible through a percutaneous incision, comprising:
- an anchor for disposition on a distal side of the internal tissue wall;
- a sealing plug for disposition on a proximal side of the internal tissue wall, the sealing plug configured to be compressed in an axial direction toward the anchor;
- a filament connected between the anchor and the sealing plug;
- a scroll gear transmission for automatically tamping the sealing plug along the filament distally towards the anchor to compress the sealing plug in the axial direction, the scroll gear transmission comprising at least two scroll gears;
- wherein a gear ratio of the scroll gear transmission changes as the at least two scroll gears rotate while engaged with each other, and wherein the gear ratio is changeable as the sealing plug passes through an outlet of a carrier tube of the closure device.

16. A tissue puncture closure device for partial insertion into and sealing of a tissue puncture in an internal tissue wall accessible through a percutaneous incision according to claim 15, further comprising a tamping device operatively connected to the scroll gear transmission, wherein the scroll gear transmission comprises:
- a storage spool onto which a proximal end of the filament is wound;
- a first scroll gear of the at least two scroll gears connected to the storage spool;
- a second scroll gear of the at least two scroll gears meshed with the first scroll gear.

17. A tissue puncture closure device for partial insertion into and sealing of a tissue puncture in an internal tissue wall accessible through a percutaneous incision according to claim 15, further comprising a tamping device operatively connected to the a scroll gear transmission, wherein the a scroll gear transmission comprises:
- a storage spool onto which a proximal end of the filament is wound;
- a first scroll gear of the at least two scroll gears connected and coaxial with the storage spool;
- a second scroll gear of the at least two scroll gears meshed with the first scroll gear;
- an output gear operatively connected to the second scroll gear and the tamping device.

18. A tissue puncture closure device for partial insertion into and sealing of a tissue puncture in an internal tissue wall accessible through a percutaneous incision according to claim 15 wherein the at least two scroll gears of the scroll gear transmission comprise:
- a first scroll gear having a gradually changing radius;
- a second scroll gear meshed with the first scroll gear, the second scroll gear having a gradually changing radius.

19. A tissue puncture closure device for partial insertion into and sealing of a tissue puncture in an internal tissue wall accessible through a percutaneous incision according to claim 15 wherein the at least two scroll gears of the scroll gear transmission comprise:
- a first scroll gear having a sudden change in radius;
- a second scroll gear meshed with the first scroll gear, the second scroll gear having a sudden change in radius.

20. A tissue puncture closure device for partial insertion into and sealing of a tissue puncture in an internal tissue wall accessible through a percutaneous incision according to claim 15, further comprising a tamping device operatively connected to the scroll gear transmission, wherein the scroll gear transmission comprises:
- a storage spool onto which a proximal end of the filament is wound;
- a scroll gearset driven by the storage spool, the scroll gearset including the at least two scroll gears;
- wherein withdrawal of the closure device from the tissue puncture with the anchor bearing against the internal tissue wall unwinds the filament from the storage spool and actuates the scroll gearset, wherein the storage spool drives the scroll gearset, and wherein the scroll gearset directly or indirectly provides a tamping force to the tamping device.

21. A tissue puncture closure device for partial insertion into and sealing of an internal tissue wall puncture, comprising:
- a filament extending from a first end of the closure device to a second end of the closure device;
- an anchor for insertion through the tissue wall puncture attached to the filament at the second end of the closure device;
- a sealing plug slidingly attached to the filament adjacent to the anchor, the sealing plug configured to be compressed in an axial direction toward the anchor;
- a tamping device adjacent to the sealing plug;
- an automatic, multi-speed scroll transmission driven by the filament and operatively connected to the tamping device for advancing the tamping device toward the sealing plug, the multi-speed scroll transmission comprising at least two scroll gears;
- wherein the gear ratio of the multi-speed scroll transmission changes as the at least two scroll gears rotate in engagement with each other, and wherein the gear ratio is changeable from a first gear ratio to a second gear ratio as the sealing plug passes through an outlet of a carrier tube of the closure device;
- wherein the tamping device compresses the sealing plug in the axial direction when the multi-speed scroll transmission operates with the second gear ratio.

22. A tissue puncture closure device for partial insertion into and sealing of an internal tissue wall puncture, comprising:
- a filament extending from a first end of the closure device to a second end of the closure device;
- an anchor for insertion through the tissue wall puncture attached to the filament at the second end of the closure device;
- a sealing plug slidingly attached to the filament adjacent to the anchor, the sealing plug configured to be compressed in an axial direction toward the anchor;
- a tamping assembly comprising a tamping device and a variable gear ratio transmission;
- wherein the variable gear ratio transmission comprises a first scroll gear having a first outside radius along a first radial degree segment, and a second outside radius along a second radial degree segment;
- wherein the first outside radius is different than the second outside radius;
- wherein the variable gear ratio transmission comprises a second scroll gear that engages the first scroll gear;
- wherein a first gear ratio of the variable gear ratio transmission changes to a second gear ratio as the sealing plug passes through an outlet of a carrier tube of the closure device to distally advance the tamping device to compress the sealing plug in the axial direction.

23. A tissue puncture closure device according to claim 22, wherein the first scroll gear has a sudden change in outside radius, and
the second scroll gear has a sudden change in outside radius.

24. A tissue puncture closure device according to claim 22, wherein the first scroll gear has a continuously changing outside radius,
and the second scroll gear has a continuously changing outside radius.

25. A method of sealing a tissue puncture in an internal tissue wall accessible through a percutaneous incision, comprising:
providing a tissue puncture closure device comprising a carrier tube, a filament extending through the carrier tube to an anchor and to a sealing plug located proximal of the anchor for disposition and anchoring about the tissue puncture, the sealing plug configured to be compressed in an axial direction toward the anchor, the tissue puncture closure device also comprising a tamping assembly comprising a tamping device and a variable gear ratio transmission that includes at least a first and second scroll gears that are engaged with each other;
inserting the tissue puncture closure device into the percutaneous incision;
deploying the anchor in the tissue puncture;
at least partially withdrawing the closure device from the percutaneous incision;
forcing the sealing plug through an outlet of the carrier tube;
automatically changing a gear ratio of the variable gear ratio transmission only after the sealing plug is forced through the outlet of the cater tube;
compressing the sealing plug in the axial direction with the tamping device after changing the gear ratio.

26. A method of sealing a tissue puncture in an internal tissue wall accessible through a percutaneous incision according to claim 25 wherein the automatically changing a gear ratio comprises providing the at least first and second scroll gears as variable radius gears.

27. A method of sealing a tissue puncture in an internal tissue wall accessible though a percutaneous incision according to claim 25 wherein automatically changing gear ratio comprises:
unwinding a filament from a spool of the tamping assembly by the withdrawing of the closure device;
driving a scroll gearset with the spool, the scroll gearset including the at least first and second scroll gears, the spool being arranged coaxially with one of the first and second scroll gears;
driving the tamping device with the scroll gearset.

28. A method of sealing a tissue puncture in an internal tissue wall accessible through a percutaneous incision according to claim 25, wherein automatically changing a gear ratio of the variable gear ratio transmission comprises rotating a first gear of the at least two scroll gears relative to a second gear of the at least two scroll gears such that the gear ratio of the variable gear ratio transmission changes.

* * * * *